United States Patent [19]

Moffett

[11] 4,073,784
[45] Feb. 14, 1978

[54] CERTAIN AS-TRIAZINO[4,3-A][1,4]BENZODIAZEPINE-1,2-DIONE COMPOUNDS

[75] Inventor: Robert Bruce Moffett, Kalamazoo, Mich.

[73] Assignee: The Upjohn Company, Kalamazoo, Mich.

[21] Appl. No.: 775,728

[22] Filed: Mar. 9, 1977

[51] Int. Cl.² .......................................... C07D 487/04
[52] U.S. Cl. .......................... 260/243.3; 260/239 BD; 260/239.3 D; 260/295 K; 424/269
[58] Field of Search ................................. 260/248 AS

[56] References Cited

U.S. PATENT DOCUMENTS

| 3,818,003 | 6/1974 | Szmuszkovicz | 260/248 AS |
|---|---|---|---|
| 3,882,112 | 5/1975 | Szmuszkovicz | 260/248 AS |
| 3,933,816 | 1/1976 | Szmuszkovicz | 260/248 AS |
| 4,016,165 | 4/1977 | Moffett | 260/248 AS |
| 4,017,492 | 4/1977 | Moffett | 260/248 AS |
| 4,028,356 | 6/1977 | Moffett | 260/248 AS |

OTHER PUBLICATIONS

Moffett, Letters on Heterocyclic Chemistry, vol. 3, pp. 3449–3456, (1976).

Primary Examiner—Alton D. Rollins
Attorney, Agent, or Firm—Hans L. Berneis

[57] ABSTRACT

Compounds of the formula V

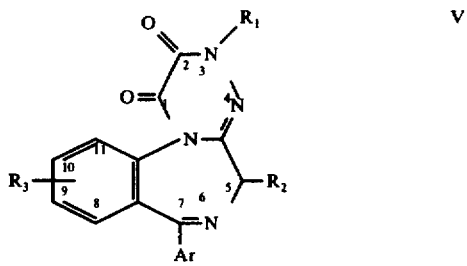

wherein $R_1$ is hydrogen, alkyl of 1 to 3 carbon atoms, inclusive;

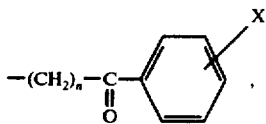

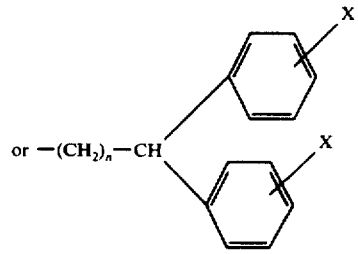

in which $n$ is 2 or 3; and X is hydrogen, fluoro or chloro; wherein $R_2$ is hydrogen, methyl or ethyl; wherein $R_3$ is hydrogen, fluoro, chloro, bromo, trifluoromethyl and nitro; and wherein Ar is phenyl, o-chlorophenyl, o-fluorophenyl, 2,6-difluorophenyl or 2-pyridyl are prepared by treating a hydrazino compound of the formula:

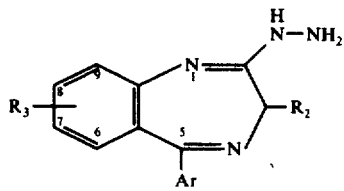

wherein Ar, $R_2$ and $R_3$ are defined as above with an alkyl oxalyl chloride and cyclizing the obtained products. Compound V, including the pharmacologically acceptable acid addition salt thereof, have sedative, anxiolytic and muscle-relaxing activity and can be used for the treatment of anxieties or muscle strains of mammals, including man.

10 Claims, No Drawings

CERTAIN AS-TRIAZINO[4,3-A][1,4]BENZODIAZEPINE-1,2-DIONE COMPOUNDS

BACKGROUND OF THE INVENTION

FIELD OF THE INVENTION

This invention is directed to new organic compounds and is particularly concerned with 1,2-dioxo-as-triazinobenzodiazepines of formula V, intermediates thereto of formula II, and the process therefor.

The novel compounds and the processes of production therefor can be illustratively represented as follows:

Method A:

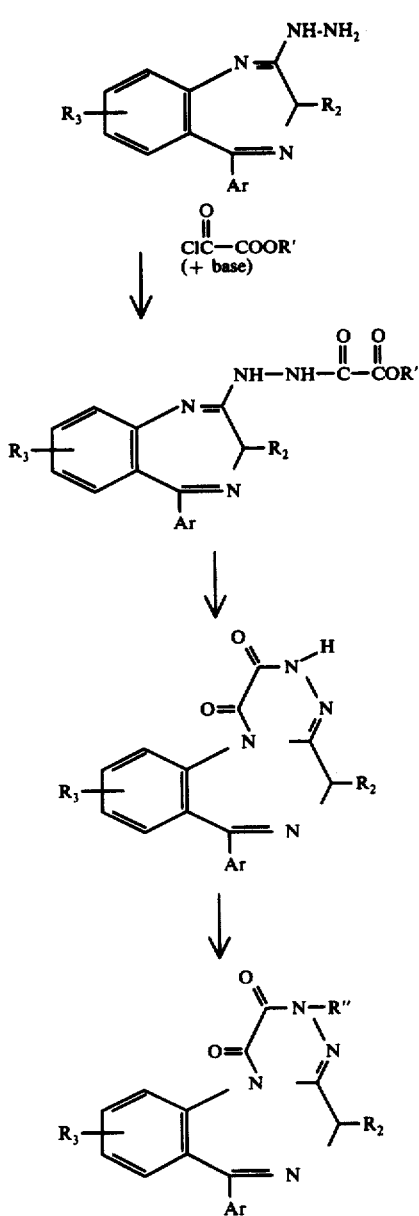

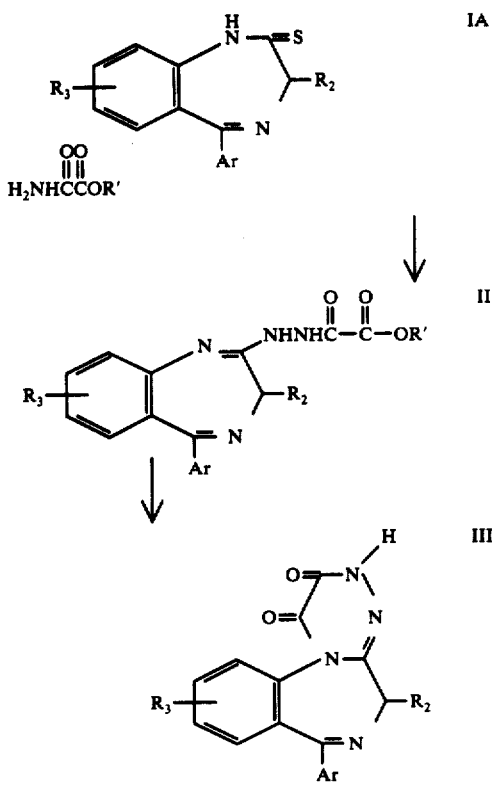

wherein R'' is alkyl of 1 to 3 carbon atoms, inclusive,

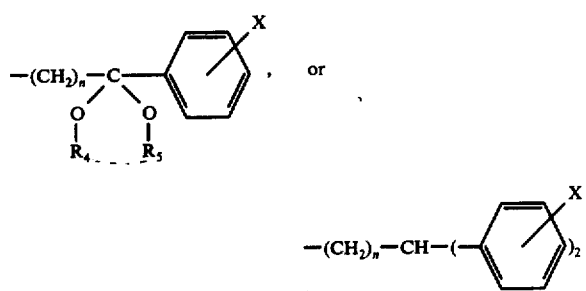

in which n is 2 or 3 and X is hydrogen, fluoro or chloro; and $R_4$ and $R_5$ are alkyl of 1 or 2 carbon atoms, or together are the group

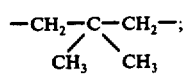

wherein $R_2$ is hydrogen, methyl or ethyl; wherein $R_3$ is hydrogen, fluoro, chloro, bromo, nitro or trifluoromethyl; wherein Ar is phenyl, o-chlorophenyl, o-fluorophenyl, 2,6-difluorophenyl or 2-pyridyl.

When the compound I VA R'' is

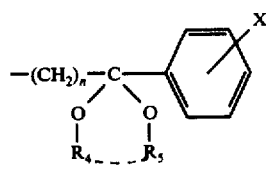

Method B:

(as above defined) the compound is submitted additionally to acid hydrolysis to give compound I VB:

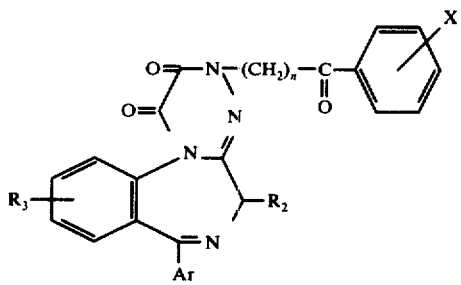

in which X, n, $R_2$, $R_3$ and Ar are defined as above.

The process of Method A of this invention comprises: treating a compound of formula I with an alkyl oxalyl chloride in the presence of a base at between 0° and −80° C. to obtain a compound of formula II; cyclizing compound II by heating it (preferably with a base) to obtain compound III [compound III corresponds to compound V in which $R_1$ is hydrogen].

When a compound of formula V is desired in which $R_1$ is other than hydrogen, compound III can be alkylated in a conventional manner, e.g., with an alkyl halide and sodium hydride or another strong base to give compound I VA above, and if compound I VA is a ketal, it is additionally hydrolized to give compound I VB.

The process of Method B consists in treating a 2-thiobenzodiazepine of the formula i with ethyl oxalylhydrazide to give the intermediate of formula II which can be cyclized by heating to a compound of formula III.

The invention claims the compounds of formulae V, the intermediates of formula II, and the pharmacologically acceptable acid addition salts thereof, and the process to make these compounds.

DESCRIPTION OF THE PREFERRED EMBODIMENT

The more preferred compounds of this invention are of the formula IIA and VA:

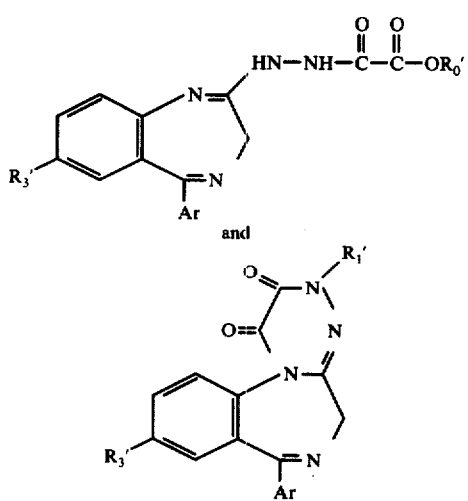

wherein $R_o'$ is methyl or ethyl, $R_1'$ is hydrogen or alkyl of 1 to 3 carbon atoms, inclusive; wherein $R_3'$ is fluoro, chloro, bromo, or trifluoromethyl; and wherein Ar is phenyl, o-chlorophenyl, o-fluorophenyl, 2,6-difluorophenyl or 2-pyridyl, and the pharmacologically acceptable acid addition salts of compound VA.

The most preferred compounds of this invention are of the formulae IIB and VB:

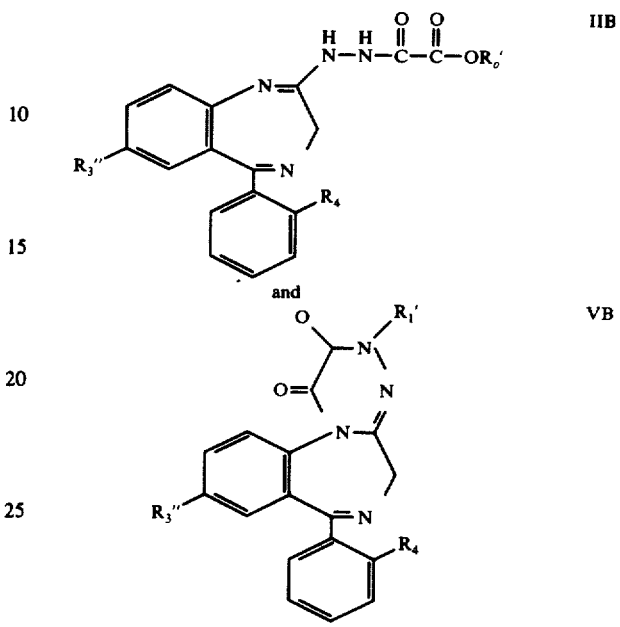

wherein $R_o'$ is methyl or ethyl; wherein $R_1'$ is hydrogen or alkyl of 1 to 3 carbon atoms, inclusive; wherein $R_3''$ is fluoro, chloro or trifluoromethyl; and wherein $R_4$ is hydrogen, chloro or fluoro, and the pharmacologically acceptable acid addition salts of compound VB.

Compounds of formula V (including VA and VB) are sedative, tranquilizing, anxiolytic, muscle-relaxing and anti-convulsive agents which are useful for treating anxieties, convulsions or strained muscles in mammals, including man.

The sedative-tranquilizing-anxiolytic activity was evaluated in compounds of formula II and V by the following test:

GAMMA-BUTYROLACTONE SLEEP POTENTIATION

Gamma-butyrolactone produces loss of righting in mice at doses higher than 400 mg./kg. intraperitoneally. At lower doses (200 mg./kg.) the mice do not lose their righting reflex unless previously treated with sub-hypnotic doses of central nervous system depressant agents. This then provides a technique to study the depressant activity of potential central nervous system agents. Method: The test compound is injected intraperitoneally, 50 mg./kg., into a group of four mice, and thirty minutes later gamma-butyrolactone is injected intraperitoneally, 200 mg./kg. (normally a sub-hypnotic dose). After ten minutes, the mice are tested for loss of righting reflex. If more than two mice show a loss of righting for one minute or more, the compound is retested at multiple dose levels.

ANTI-CONVULSION TEST

Protection Against Bicucullin-Induced Tonic Extensor Convulsions

In this procedure, groups of four (4) Carworth Farms male mice, weighing 18–22 g. each, are injected intraperitoneally with the test agent prepared in 0.25 percent methylcellulose. Thirty minutes later, bicucullin is injected intravenously at 1 mg./kg. Bicucullin is solubilized in 1N hydrochloric acid and diluted to a concentration of 1-4 mg./ml. with physiological saline which is adjusted to a final pH of 5-6 before injection. Mice are observed for 5 minutes after bicucullin injection. A compound is considered to be active if it protects at least 2 of the 4 mice from tonic extensor convulsions during this period. Active compounds are retested using multiple dose levels decreasing 0.3 or 0.5 log intervals and the number of mice failing to convulse is used as a quantal response to calculate the $ED_{50}$ (Spearman and Karber: Finney, D. J. Statistical Method of Biological Assay, Hafner Publ. Co., N.Y., p. 524, 1952). This procedure is a useful test for detecting compounds with minor tranquilizer or sedative activity.

ANTI-CONVULSANT MUSCULAR RELAXING ACTIVITY BY THE PENTYLENE-TETRAZOL (METRAZOL) TEST

Metrazol Induced Convulsion Test

The test compound is injected intraperitoneally (50 mg./kg.) into groups of four (4) mice at multiple dose levels decreasing in 0.3 log intervals. Thirty minutes later Metrazol is injected subcutaneously (at the nape of the neck), 85 mg./kg. Fifteen minutes later a set of keys is rattled over the cage to induce the clonic convulsions. The number of mice protected against convulsions and death is recorded.

PROLONGATION OF HYPOXIC SURVIVAL

Pretreatment of mice exposed to the stress of progressive hypoxia and hypercapnia with anxiolytics results in a prolongation of survival. This effect appears to be relatively specific. Since tolerance does not appear to develop to the clinical anxiolytic effects of benzodiazepines, the hypoxic survivial test is a useful screening technique for anxiolytic drugs.

Male CF-1 derived mice were used in these studies. Thirty minutes after intraperitoneal pretreatment (test agent suspended in 0.25 percent methylcellulose or vehicle alone, 1 cc./100 gm. body weight) the mice were placed singly in 125 ml. erlenmeyer flasks. The receptacles were tightly stoppered and the survival time (time from stoppering to the last respiratory effort) of each animal noted. Each compound was tested at three or more doses spaced at 0.3 log intervals. Six mice were used per dose with six vehicle injected controls run simultaneously. The mean (15-18 minutes) and standard deviation (1-2 minutes) of the survival time for the vehicle treated mice were used to convert the data to a quantal form in the following manner. All survival times that differed from the mean of the controls by more than two standard deviations were scored as a drug effect. $ED_{50}$ were calculated by the method of Spearman and Karber (Finney, D. J., Statistical Method in Biological Assay, Hafner Publ. Co., N.Y., 1952).

The compound of formula V, wherein $R_1$ is hydrogen, was positive in all tests and about equal to chlordiazepoxide (Librium ®). The compounds of formula V wherein $R_1$ is substituted by alkyl, alkylaryl or the like are less active as sedatives and anxiolytic agents, did not give on all four tests described above positive results when tested at up to 50 mg./kg.

Thus, compounds of formula V as well as the pharmaceutically acceptable acid addition salts thereof are useful for tranquilization, sedation, treating anxieties, and also useful as anti-convulsant and muscle-relaxants in mammals and birds.

The compounds of formula II had similar activities but lesser than those of compounds of formula V. The importance of the compounds of formula II is their use as intermediates.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers, such as, carbohydrates (lactose), proteins, lipids, calcium phosphate, corn starch, stearic acid, methylcellulose and the like, may be used as carriers or for coating purposes. Water or oil, e.g., coconut oil, sesame oil, safflower oil, cottonseed oil, peanut oil, may be used for preparing solutions or suspensions of the active drug. Sweetening, coloring and flavoring agents may be added.

For mammals and birds, food premixes with starch, oatmeal, dried fishmeat, fishmeal, flour and the like, can be prepared.

The compounds of formula II and V can be used in dosages of 0.05-5 mg./kg./day; preferably in unit dosages of 0.2-2.0 mg./kg/day in oral or injectable preparations as described above, to alleviate tension and anxiety, muscle spasm or convulsions in mammals, including man, or birds.

The starting materials of formula I of this invention, with a 5-phenyl- or substituted phenyl groups, are known in the art, e.g., from Canadian Patent No. 908,657. The compounds of formula 1 which have a 5-pyridyl group are prepared as described in U.S. Pat. No. 3,996,230.

In carrying out the process of Method A of this invention, a compound of formula I is reacted with an alkyl oxalylchloride compound, in which the alkyl group is of 1 to 3 carbon atoms. Ethyl oxalylchloride is preferred. The reaction is preferably carried out in the presence of a proton acceptor. Bases useful for this purpose are triethylamine, diisopropylethylamine, pyridine, picolines, sodium bicarbonate, calcium carbonate or the like. In the preferred embodiment of this invention an inert organic solvent is use, e.g., dioxane, tetrahydrofuran, diethyl ether, dichloromethane or the like. The reaction temperature is kept between 0° and −80°. The reaction period is between 5 minutes and 3 hours. The molar proportions between compound 1, the base and the alkyl oxalyl chloride are about 1:1:1 or preferably at 10 percent mole equivalent excess of the reagents, base and alkyl oxalyl halide, it used. After the reaction is terminated, the product, a compound of formula II, is recovered by conventional means, such as, removing the solvent, extraction, chromatography and recrystallization.

compound II is heated to between 80°-150°, preferably in pyridine, picolines or the like, to cyclize to the corresponding compound III. The reaction period is between ½ to 6 hours.

After termination of the reaction, the compound III is recovered and purified by standard procedures, e.g., evaporation of the solvent, extraction, crystallization and chromatography.

Compound III can be alkylated in conventional manner, e.g., with alkyl halides in the presence of a strong base, e.g., sodium hydride, sodium or potassium alkoxide, e.g., potassium ethoxide, sodium methoxide, or with lithium diisopropylamide or the like. It an alkyl chloride or bromide is used, potassium iodide may be added.

Instead of alkyl halides, halogenated aralkyl can be used, e.g., a ketal of 1-[3-(p-fluorobenzoyl)-propyl]chloride, 3,3-di-(p-fluorophenyl)butyl chloride, and the like. The product is isolated and purified in conventional manner, e.g., evaporating the solvent, washing and extracting the residue, crystallization, and chromatography providing compounds of formula I VA in purified form.

If the compound of formula I VA contains a ketal group, this group is removed by a conventional acid hydrolysis to provide compounds of formula I VB.

The following examples are illustrative of the process and the compounds of the present invention, but are not to be limiting.

EXAMPLE 1:
2-(7-Chloro-5-phenyl-3H-1,4-benzodiazepin-2-yl)hydrazide of oxalic acid ethyl ester A solution of 1.42 g. (0.005 mole) of 7-chloro-2-hydrazino-5-phenyl-3H-1,4-benzodiazepine and 0.8 ml. (0.0055 mole) of dried triethylamine in 25 ml. of tetrahydrofuran, under nitrogen, was cooled to $-80°$ C. and a solution of 0.615 ml. (0.0055 mole) of ethyl oxalyl chloride in 25 ml. of tetrahydrofuran was added dropwise with stirring during 20 minutes. After stirring at $-80°$ C. for 1 hour and at room temperature for 2 hours the mixture was evaporated in vacuo, well mixed with ice, sodium bicarbonate and methylene chloride. Part of the product remained as a crystalline solid and more was obtained by concentration of the methylene chloride solution yielding 1.03 (53.5 percent) of 2-(7-chloro-5-phenyl-3H-1,4-benzodiazepin-2-yl)hydrazide of oxalic acid ethyl ester as a white solid. An analytical sample of this solid, recrystallized from ethanol, had a melting point of 173°-175° C. with decomposition.

Anal. Calcd. for $C_{19}H_{17}ClN_4O_3$: C, 59.30; H, 4.45; Cl, 9.21; N, 14.56 Found: C, 59.26; H, 4.41; Cl, 9.21; N, 14.44

EXAMPLE 2:
9-Chloro-3,5-dihydro-7-phenyl-as-triazino-[4,3-a][1,4]benzodiazepine-1,2-dione A solution of 1.0 g. (0.0026 mole) of 2-(7-chloro-5-phenyl-3H-1,4-benzodiazepin-2-yl)hydrazide of oxalic acid ethyl ester in 25 ml. of dried pyridine was stirred, in a nitrogen atmosphere, under reflux during 2 hours and allowed to stand at room temperature (20°-23° C.) overnight. Evaporation in vacuo below 45° C. gave a gum which was dissolved in methylene chloride, filtered, again evaporated, and crystallized from ethyl acetate yielding 0.76 g. (86 percent) of 9-chloro-3,5-dihydro-7-phenyl-as-triazino-[4,3-a][1,4]benzodiazepine-1,2-dione in the form of white crystals of melting point 260°-263° C. with decomposition. These crystals were recrystallized from 2-propanol and then from dioxane having a melting point of 289°-294° C. (dec.). All samples contained solvent of crystallization and all melting points showed sintering much below the decomposition.

Anal. Calcd. for $C_{17}H_{11}ClN_4O_2$: C, 60.28; H, 3.27; Cl, 10.46; N, 16.54 Found: C, 60.18; H; 3.18; Cl, 10.45; N, 16.47

EXAMPLE 3
9-Chloro-3,5-dihydro-3-methyl-7-phenyl-as-triazino[4,3-a][1,4]benzodiazepine-1,2-dione To a solution of 0.678 g. (0.002 mole) of 9-chloro-3,5-dihydro-7-phenyl-as-triazino[4,3-a][1,4]benzodiazepine-1,2-dione in 30 ml. of tetrahydrofuran, under nitrogen, was added with stirring 0.1 g. (0.0022 mole) of 50 percent sodium hydride in mineral oil. After 5 minutes, 0.62 ml. (0.01 mole) of methyl iodide was added, dropwise, during 10 minutes. The solution was stirred for 3 hours, evaporated in vacuo and well shaken with ice water and ether. The resulting crystalline solid was collected, washed with water and ether, and dried yielding 0.48 g. (68 percent) of 9-chloro-3,5-dihydro-3-methyl-7-phenyl-as-triazino-[4,3-a][1,4]benzodiazepine-1,2-dione of melting point 261°-265° C. A sample for analysis was recrystallized from methanol, having a melting point 266°-267° C.

Anal. Calcd. for $C_{18}H_{13}ClN_4O_2$: C, 61.28; H, 3.71; Cl, 10.05; N, 15.88 Found: C, 61.23; H, 3.70; Cl, 10.15; N, 16.15

EXAMPLE 4
9-Chloro-3,5-dihydro-3-[3-(p-fluorobenzoyl)propyl]-7-phenyl-as-triazino[4,3-a][1,4]benzodiazepine-1,2-dione A. 9-Chloro-3-[3-[2-(p-fluorophenyl)-5,5-dimethyl-1,3-dioxan-2-yl]propyl]-3,5-dihydro-7-phenyl-as-triazino[4,3-a][1,4]benzodiazepine-1,2-dione.

To a solution of 0.678 g. (0.002 mole) of 9-chloro-3,5-dihydro-7-phenyl-as-triazino[4,3-a][1,4]benzodiazepine-1,2-dione in 15 ml. of dimethylformamide, under nitrogen, was added with stirring 0.11 g. (0.0025 mole) of 50 percent sodium hydride in mineral oil. After stirring for 30 minutes 0.42 g. (0.0025 mole) of potassium iodide and 0.63 g. (0.0022 mole) of 2-(3-chloropropyl)-2-(p-fluorophenyl)-2,2-dimethyl-1,3-dioxane were added. The mixture was stirred for 3½ hours on a steam bath and allowed to stand at room temperature overnight. The mixture was evaporated in vacuo and the residue was shaken with ice water and ether. The ether solution was washed with sodium bicarbonate, water, saturated sodium chloride solution, and dried over anhydrous sodium sulfate. After filtration the solution was evaporated, the residue was crystallized from ether, and dried in vacuo, yielding 0.54 (46 percent of 9-chloro-3-[3-[2-(p-fluorophenyl)-5,5-dimethyl-1,3-dioxane-2-yl]propyl]-3,5-dihydro-7-phenyl-as-triazino[4,3-a][1,4]benzodiazepine-1,2-dione of melting point 155°-160° C.

Anal. Calcd. for $C_{32}H_{30}ClFN_4O_4$: C, 65.25; H, 5.13; Cl, 6.02; F, 3.23; N, 9.51 Found: C, 65.49; H, 5.33; Cl, 6.01; F, 3.39; N, 9.50

B. 9-Chloro-3,5-dihydro-3-[3-(p-fluorobenzoyl)propyl]-7-phenyl-as-triazino[4,3-a][1,4]benzodiazepine-1,2-dione.

9-Chloro-3-[3-[2-(p-fluorophenyl)-5,5-dimethyl-1,3-dioxan-2-yl]-3,5-dihydro-7-phenyl-as-triazino[4,3-a][1,4]benzodiazepine-1,2-dione as prepared above was dissolved in 50 ml of methanol, filtered and acidified (pH 1.3) with 5 ml. of 1.5 N hydrochloric acid. After standing at room temperature for 95 minutes, the mixture was neutralized with 50 ml. of ice water and 20 ml. of 5 percent aqueous sodium bicarbonate. The precipitate was collected, washed with water and dried giving a tan solid which was chromatographed on silica gel eluting with 70 percent hexane, 25 percent methylene chloride, 5 percent 2-propanol. The product was dissolved in 2-propanol and concentrated yielding 0.31 g. (31 percent) of 9-chloro-3,5-dihydro-3-[3-(p-fluorobenzoyl)propyl]-7-phenyl-as-triazino-[4,3-a][1,4]benzodiazepine-1,2-dione as a solid with no distinct melting point. Tlc ($SiO_2$, 60 percent EtOAc/cyclohexane) showed only one spot (Rf 1.5); ir (nujol): 1725 1680 (C=O), 1635, 1600 (C=N), 1505 (C=C), 1400, 1320, 1225, 1155, 830, 705, 695 (other).

Anal. Calcd. for $C_{27}H_{20}ClFN_4O_3$: C, 64.48; H, 4.01; Cl, 7.05; F, 3.78; N, 11.14 Found: C, 64.24; H, 4.26; Cl, 6.95; F, 3.90; N, 10.91

EXAMPLE 5

2-[7-Chloro-5-(o-chlorophenyl)3H-1,4-benzodiazepin-2-yl]hydrazide of oxalic acid ethyl ester In the manner given in Example 1 a solution of 7-chloro-2-hydrazino-5-(o-chlorophenyl)-3H-1,4-benzodiazepine and triethylamino in tetrahydrofuran can be reacted at −80° C. with ethyl oxalyl chloride in tetrahydrofuran to give 2-[7-chloro-5-(o-chlorophenyl)-3H-1,4-benzodiazepin-2-yl]hydrazide of oxalic acid ethyl ester.

EXAMPLE 6

9-Chloro-3,5-dihydro-7-(o-chlorophenyl)-astriazino[4,3-a][1,4]benzodiazepine-1,2-dione In the manner given in Example 2, a solution of 2-[7-chloro-5-(o-chlorophenyl)-3H-1,4-benzodiazepin-2-yl]-hydrazine of oxalic acid ethyl ester in pyridine can be heated to reflux to give 9-chloro-3,5-dihydro-7-(o-chlorophenyl)as-triazino[4,3-a][1,4]benzodiazepine-1,2-dione.

EXAMPLE 7

9-Chloro-3,5-dihydro-3-methyl-7-(o-chlorophenyl)-as-triazino[4,3-a][1,4]benzodiazepine-1,2-dione In the manner given in Example 3, to a solution of 9-chloro-3,5-dihydro-7-(o-chlorophenyl)-as-triazino[4,3-a][1,4]benzodiazepine-1,2-dione in tetrahydrofuran can be added sodium hydride and after 5 minutes methyl iodide dropwise. After stirring the mixture for four hours 9-chloro-3,5-dihydro-3-methyl-7-(o-chlorophenyl)-as-triazino[4,3-a][1,4]benzodiazepine-1,2-dione can be obtained.

EXAMPLE 8

9-Chloro-3,5-dihydro-3-[[4,4-di-(p-chlorophenyl)-butan]-1-yl]-7-(o-chlorophenyl)-as-triazino[4,3-a][1,4]benzodiazepine-1,2-dione In the manner given in Example 4A, 9-chloro-3,5-dihydro-7-(o-chlorophenyl)-as-triazino[4,3-a][1,4]benzodiazepine-1,2-dione in diemthylformamide can be treated first with sodium hydride in mineral oil, and then with potassium iodide and 1-chloro-4,4-di(p-chlorophenyl)-butane to give 9-chloro-3-[[4,4-di(p-chlorophenyl)butane]-1-yl]-3,5-dihydro-7-(o-chlorophenyl)-as-triazino[4,3-a][1,4]benzodiazepine-1,2-dione.

EXAMPLE 9

2-(7-Fluoro-5-phenyl-3H-1,4-benzodiazepin-2-yl)hydrazide of oxalic acid methyl ester In the manner given in Example 1 a solution of 7-fluoro-2-hydrazino-5-phenyl-3H-1,4-benzodiazepine and triethylamine in tetrahydrofuran can be reacted at −80° C. with methyl oxalyl chloride in tetrahydrofuran to give 2-(7-fluoro-5-phenyl-3H-1,4-benzodiazepin-2-yl)hydrazide of oxalic acid methyl ester.

EXAMPLE 10

9-Fluoro-3,5-dihydro-7-phenyl-as-triazino-[4,3-a][1,4]benzodiazepine-1,2-dione

In the manner given in Example 2, a solution of 2-(7-fluoro-5-phenyl-3H-1,4-benzodiazepin-2-yl)hydrazide of oxalic acid methyl ester in pyridine can be heated to reflux to give 9-fluoro-3,5-dihydro-7-phenyl-as-triazino[4,3-a][1,4]benzodiazepine-1,2-dione.

EXAMPLE 11

9-Fluoro-3,5-dihydro-3-ethyl-7-phenyl-as-triazino[4,3-a][1,4]benzodiazepine-1,2-dione In the manner given in Example 3 to a solution of 9-fluoro-3,5-dihydro-7-phenyl-as-triazino[4,3-a]-[1,4]benzodiazepine-1,2-dione in tetrahydrofuran can be added sodium hydride and after 5 minutes, ethyl iodide dropwise. After stirring the mixture for 4 hours 9-fluoro-3,5-dihydro-3-ethyl-7-phenyl-as-triazino[4,3-a][1,4]benzodiazepine-1,2-dione can be obtained.

EXAMPLE 12

2-[7-Nitro-3-methyl-5-(o-chlorophenyl)3H-1,4-benzodiazepin-2-yl]hydrazide of oxalic acid ethyl ester In the manner given in Example 1 a solution of 7-nitro-2-hydrazino-3-methyl-5-(o-chlorophenyl)-3H-1,4-benzodiazepine and triethylamine in tetrahydrofuran can be reacted at −80° C. with ethyl oxalyl chloride in tetrahydrofuran to give 2-[7-nitro-3-methyl-5-(o-chlorophenyl)-3H-1,4-benzodiazepin-2-yl]hydrazide of oxalic acid ethyl ester.

EXAMPLE 13

9-Nitro-3,5-dihydro-5-methyl-7-(o-chlorophenyl)-as-triazino[4,3-a][1,4]benzodiazepine-1,2-dione In the manner given in Example 2, a solution of 2-[7-nitro-3-methyl-5-(o-chlorophenyl-3H-1,4-benzodiazepin-2-yl]hydrazide of oxalic acid ethyl ester in pyridine can be heated to reflux to give 9-nitro-3,5-dihydro-5-methyl-7-(o-chlorophenyl)-as-triazino[4,3-a]-[1,4]benzodiazepine-1,2-dione.

EXAMPLE 14

9-Nitro-3,5-dihydro-5-methyl-3-propyl-7-(o-chlorophenyl)-as-triazino[4,3-a][1,4]benzodiazepine-1,2-dione In the manner given in Example 3 to a solution of 9-nitro-3,5-dihydro-5-methyl-7-(o-chlorophenyl)-as-triazino[4,3-a][1,4]benzodiazepine-1,2-dione in tetrahydrofuran can be added sodium hydride and after 5 minutes propyl iodide dropwise. After stirring the mixture for 4 hours 9-nitro-3,5-dihydro-5-methyl-3-propyl-7-(o-chlorophenyl)-as-triazino[4,3-a][1,4]-benzodiazepine-1,2-dione can be obtained.

EXAMPLE 15

2-[7-Chloro-5-(2,6-difluorophenyl)3H-1,4-benzodiazepin-2-yl]hydrazide of oxalic acid ethyl ester In the manner given in Example 1 a solution of 7-chloro-2-hydrazino-5-(2,6-difluorophenyl)-3H-1,4-benzodiazepine and triethylamine in tetrahydrofuran can be reacted at −80° C. with ethyl oxalyl chloride in tetrahydrofuran to give 2-[7-chloro-5-(2,6-difluorophenyl)-

3H-1,4-benzodiazepin-2-yl]hydrazide of oxalic acid ethyl ester.

EXAMPLE 16

9-Chloro-3,5-dihydro-7-(2,6-difluorophenyl)-as-triazino[4,3-a][1,4]benzodiazepine-1,2-dione In the manner given in Example 2, a solution of 2-[7-chloro-5-(2,6-difluorophenyl)-3H-1,4-benzodiazepin-2-yl]hydrazide of oxalic acid ethyl ester in pyridine can be heated to reflux to give 9-chloro-3,5-dihydro-7-(2,6-difluorophenyl)-as-triazino[4,3-a][1,4]benzodiazepine-1,2-dione.

EXAMPLE 17

9-Chloro-3,5-dihydro-3-methyl-7-(2,6-di-fluorophenyl)-as-triazino[4,3-a][1,4]benzodiazepine-1,2-dione In the manner given in Example 3 to a solution of 9-chloro-3,5-dihydro-7-(2,6-difluorophenyl)-as-triazino-[4,3-a][1,4]benzodiazepine-1,2-dione in tetrahydrofuran can be added sodium hydride and after 5 minutes methyl bromide dropwise. After stirring the mixture for 6 hours 9-chloro-3,5-dihydro-3-methyl-7-(2,6-difluorophenyl)-as-triazino[4,3-a][1,4]benzodiazepine-1,2-dione can be obtained.

EXAMPLE 18

9-Chloro-3,5-dihydro-3-[3-(p-fluorobenzoyl)propyl]-7-(2,6-difluorophenyl)-as-triazino[4,3-a][1,4]benzodiazepine-1,2-dione In the manner given in Example 4A, 9-chloro-3,5-dihydro-7-(2,6-difluorophenyl)-as-triazino[4,3-a][1,4]-benzodiazepine-1,2-dione in dimethylformamide can be treated first with sodium hydride in mineral oil, and then with potassium iodide and 2-(3-chloropropyl)-2-(p-fluorophenyl)-2,2-dimethyl-1,3-dioxane to give 9-chloro-3-[3-[2-(p-fluorophenyl)-5,5-dimethyl-1,3-dioxane-2-yl]propyl]-3,5-dihydro-7-(2,6-difluorophenyl)-as-triazino[4,3-a][1,4]benzodiazepine-1,2-dione.

In the manner given in Example 4B, 9-chloro-3-[3-[2-(p-fluorophenyl)-5,5-dimethyl-1,3-dioxane-2-yl]-propyl]-3,5-dihydro-7-(2,6-difluorophenyl)-as-triazino-[4,3-a][1,4]benzodiazepine-1,2-dione can be hydrolyzed in aqueous methanolic hydrogen chloride solution to give 9-chloro-3,5-dihydro-3-[3-(p-fluorobenzoyl)-propyl]-7-(2,6-difluorophenyl)-as-triazino[4,3-a][1,4]benzodiazepine-1,2-dione.

EXAMPLE 19

2-[5-(o-Chlorophenyl)3H-1,4-benzodiazepin-2-yl]hydrazide of oxalic acid ethyl ester In the manner given in Example 1 a solution of 2-hydrazino-5-(o-chlorophenyl)-3H-1,4-benzodiazepine and triethylamine in tetrahydrofuran can be reacted at −80° C. with ethyl oxalyl chloride in tetrahydrofuran to give 2-[5-(o-chlorophenyl)-3H-1,4-benzodiazepine-2-yl]hydrazide of oxalic acid ethyl ester.

EXAMPLE 20

3,5-Dihydro-7-(o-chlorophenyl)-as-triazino[4,3-a][1,4]benzodiazepine-1,2-dione

In the manner given in Example 2, a solution of 2-[5-(o-chlorophenyl)-3H-1,4-benzodiazepin-2-yl]hydrazide of oxalic acid ethyl ester in pyridine can be heated to reflux to give 3,5-dihydroy-7-(o-chlorophenyl)-as-triazino[4,3-a][1,4]benzodiazepine-1,2-dione.

EXAMPLE 21

3,5-Dihydro-3-ethyl-7-(o-chlorophenyl)-as-triazino[4,3-a][1,4]benzodiazepine-1,2-dione In the manner given in Example 3 to a solution of 3,5-dihydro-7-(o-chlorophenyl)-as-triazino[4,3-a][1,4]-benzodiazepine-1,2-dione in tetrahydrofuran can be added sodium hydride and after 5 minutes ethyl iodide dropwise. After stirring the mixture for 4 hours 3,5-dihydro-3-ethyl-7-(o-chlorophenyl)-as-triazino[4,3-a][1,4]benzodiazepine-1,2-dione can be obtained.

EXAMPLE 22

2-[7-bromo-5-(2-pyridyl)-3H-1,4-benzodiazepin-2-yl]hydrazide of oxalic acid ethyl ester In the manner given in Example 1 a solution of 7-bromo-2-hydrazino-5-(2-pyridyl)-3H-1,4-benzodiazepine and triethylamine in tetrahydrofuran can be reacted at −80° C. with ethyl oxalyl chloride in tetrahydrofuran to give 2-[7-bromo-5-(2-pyridyl)-3H-1,4-benzodiazepin-2-yl]hydrazide of oxalic acid ethyl ester.

EXAMPLE 23

9-Bromo-3,5-dihydro-7-(2-pyridyl)-as-triazino[4,3-a][1,4]benzodiazepine-1,2-dione In the manner given in Example 2, a solution of 2-[7-bromo-5-(2-pyridyl)-3H-1,4-benzodiazepin-2-yl]hydrazide of oxalic acid ethyl ester in pyridine can be heated to reflux to give 9-bromo-3,5-dihydro-7-(2-pyridyl)-as-triazino[4,3-a][1,4]benzodiazepine-1,2-dione.

EXAMPLE 24

9-Bromo-3,5-dihydro-3-methyl-7-(2-pyridyl)-as-triazino[4,3-a][1,4]benzodiazepine-1,2-dione In the manner given in Example 3, to a solution of 0.002 mole of 9-bromo-3,5-dihydro-3-methyl-7-(2-pyridyl)-as-triazino[4,3-a][1,4]benzodiazepine-1,2-dione in tetrahydrofuran can be added sodium hydride and after 5 minutes 0.0022 mole of methyl iodide dropwise. After stirring the mixture for 4 hours 9-bromo-3,5-dihydro-3-methyl-7-(2-pyridyl)-as-triazino[4,3-a][1,4]benzodiazepine-1,2-dione can be obtained.

EXAMPLE 25

2-[7-fluoro-3-ethyl-5-(o-fluorophenyl)-3H-1,4-benzodiazepin-2-yl]hydrazide of oxalic acid ethyl ester In the manner given in Example 1, a solution of 7-fluoro-2-hydrazino-5-(o-fluorophenyl)-3H-1,4-benzodiazepine and triethylamine in tetrahydrofuran can be reacted at −80° C. with ethyl oxalyl chloride in tetrahydrofuran to give 2-[7-fluoro-3-ethyl-5-(o-fluorophenyl)-3H-1,4-benzodiazepin-2-yl]hydrazide of oxalic acid ethyl ester.

EXAMPLE 26

9-Fluoro-3,5-dihydro-5-ethyl-7-(o-fluorophenyl)-as-triazino[4,3-a][1,4]benzodiazepine-1,2-dione In the manner given in Example 2, a solution of 2-[7-fluoro-3-ethyl-5-(o-fluorophenyl)-3H-1,4-benzodiazepin-2-yl]hydrazide of oxalic acid ethyl ester in pyridine can be heated to reflux to give 9-fluoro-5-ethyl-3,5-dihydro-7-(o-fluorophenyl)-as-triazino[4,3-a][1,4]benzodiazepine-1,2-dione.

EXAMPLE 27

9-Fluoro-3,5-dihydro-3,5-diethyl-7-(o-fluorophenyl)-as-triazino[4,3-a][1,4]benzodiazepine-1,2-dione In the manner given in Example 3 to a solution of 9-fluoro-3,5-dihydro-5-ethyl-7-(o-fluorophenyl)-as-triazino[4,3-a][1,4]benzodiazepine-1,2-dione in tetrahydrofuran can be added sodium hydride and after 5 minutes ethyl iodide dropwise. After stirring the mixture for 4 hours, 9-fluoro-3,5-dihydro-3,5-diethyl-7-(o-fluorophenyl)-as-triazino[4,3-a][1,4]benzodiazepine-1,2-dione can be obtained.

EXAMPLE 28

2-[7-Trifluoromethyl-5-(o-chlorophenyl-3H-1,4-benzodiazepin-2-yl]hydrazide of oxalic acid ethyl ester In the manner given in Example 1 a solution of 7-trifluoromethyl-2-hydrazino-5-(o-chlorophenyl)-3H-1,4-benzodiazepine and triethylamine in tetrahydrofuran can be reacted at −80° C. with ethyl oxalyl chloride in tetrahydrofuran to give 2-[7-trifluoromethyl-5-(o-chlorophenyl)-3H-1,4-benzodiazepin-2-yl]hydrazide of oxalic acid ethyl ester.

EXAMPLE 29

9-Trifluoromethyl-3,5-dihydro-7-(o-chloro-phenyl-as-triazino[4,3-a][1,4]benzodiazepine-1,2-dione In the manner given in Example 2 a solution of 2-[7-trifluoromethyl-5-(o-chlorophenyl)-3H-1,4-benzodiazepin-2-yl]hydrazide of oxalic acid ethyl ester in pyridine can be heated to reflux to give 9-trifluoromethyl-3,5-dihydro-7-(o-chlorophenyl)-as-triazino[4,3-a][1,4]benzodiazepine-1,2-dione.

EXAMPLE 30

9-Trifluoromethyl-3,5-dihydro-3-methyl-7-(o-chlorophenyl)-as-triazino[4,3-a][1,4]benzodiazepine-1,2-dione In the manner given in Example 3 to a solution of 9-trifluoromethyl-3,5-dihydro-3-methyl-7-(o-chlorophenyl)-as-triazino[4,3-a][1,4]benzodiazepine-1,2-dione in tetrahydrofuran can be added sodium hydride and after 5 minutes methyl iodide dropwise. After stirring the mixture for 4 hours 9-trifluoromethyl-3,5-dihydro-3-methyl-7-(o-chlorophenyl)-as-triazino[4,3-a][1,4]benzodiazepine-1,2-dione can be obtained.

EXAMPLE 31

9-Trifluoromethyl-3,5-dihydro-3-[3-(p-fluorobenzoyl)-propyl]-7-(o-chlorophenyl)-as-triazino[4,3-a][1,4]benzodiazepine-1,2-dione In the manner given in Example 4A, 9-trifluoromethyl-3,5-dihydro-7-(o-chlorophenyl)-as-triazino[4,3-a][1,4]-benzodiazepine-1,2-dione in dimethylformamide can be treated first with sodium hydride in mineral oil, and then with potassium iodide and 2-(3-chloropropyl)-2-(p-fluorophenyl)-2,2-dimethyl-1,3-dioxane to give 9-trifluoromethyl-3-[3-[2-(p-fluorophenyl)-5,5-dimethyl-1,3-dioxane-2-yl]propyl]-3,5-dihydro-7-(o-chlorophenyl)-as-triazino[4,3-a][1,4]benzodiazepine-1,2-dione.

In the manner given in Example 4B, 9-trifluoromethyl-3-[3-[2-(p-fluorophenyl)-5,5-dimethyl-1,3-dioxane-2-yl]propyl]-3,5-dihydro-7-(o-chlorophenyl)-as-triazino[4,3-a][1,4]benzodiazepine-1,2-dione can be hydrolyzed in aqueous methanolic hydrogen chloride solution to give 9-trifluoromethyl-3,5-dihydro-3-[3-(o-fluorobenzoyl)propyl]-7-(o-chlorophenyl)-as-triazino[4,3-a][1,4]benzodiazepine-1,2-dione.

EXAMPLE 32

2-[8-Chloro-5-(o-fluorophenyl)-3H-1,4-benzodiazepin-2-yl]hydrazide of oxalic acid ethyl ester In the manner given in Example 1 a solution of 8-chloro-2-hydrazino-5-(o-fluorophenyl)-3H-1,4-benzodiazepine and triethylamine in tetrahydrofuran can be reacted at −80° C. with ethyl oxalyl chloride in tetrahydrofuran to give 2-[8-chloro]-5-(o-fluorophenyl)-3H-1,4-benzodiazepin-2-yl]hydrazide of oxalic acid ethyl ester.

EXAMPLE 33

10-Chloro-3,5-dihydro-7-(o-fluorophenyl)-as-triazino[4,3-a][1,4]benzodiazepine-1,2-dione In the manner given in Example 2, a solution of 2-[8-chloro-5-(o-fluorophenyl)-3H-1,4-benzodiazepin-2-yl]hydrazide of oxalic acid ethyl ester in pyridine can be heated to reflux to give 10-chloro-3,5-dihydro-7-(o-fluorophenyl)-as-triazino[4,3-a][1,4]benzodiazepine-1,2-dione.

EXAMPLE 34

10-Chloro-3,5-dihydro-3-isopropyl-7-(o-fluorophenyl)-as-triazino[4,3-a][1,4]benzodiazepine-1,2-dione In the manner given in Example 3 to a solution of 10-chloro-3,5-dihydro-7-(o-fluorophenyl)-as-triazino[4,3-a][1,4]benzodiazepine-1,2-dione in tetrahydrofuran can be added sodium hydride and after 5 minutes isopropyl iodide dropwise. After stirring the mixture for 4 hours 10-chloro-3,5-dihydro-3-isopropyl-7-(o-fluorophenyl)-as-triazino[4,3-a][1,4]benzodiazepine-1,2-dione can be obtained.

EXAMPLE 35

10-Chloro-3,5-dihydro-3-[3-(p-fluorobenzoyl)propyl]-7-(o-fluorophenyl)-as-triazino[4,3-a][1,4]benzodiazepine-1,2-dione In the manner given in Example 4A, 10-chloro-3,5-dihydro-7-(o-fluorophenyl)-as-triazino[4,3-a][1,4]benzodiazepine-1,2-dione in dimethylformamide can be treated first with sodium hydride in mineral oil, and then with potassium iodide and 2-(3-chloropropyl)-2-(p-fluorophenyl)-2,2-dimethyl-1,3-dioxane to give 10-chloro-3-[3-[2-(p-fluorophenyl)-5,5-dimethyl-1,3-dioxane-2-yl]propyl]-3,5-dihydro-7-(o-fluorophenyl)-as-triazino[4,3-a][1,4]benzodiazepine-1,2-dione.

In the manner given in Example 4B, 10-chloro-3-[3-[2-(p-fluorophenyl)-5,5-dimethyl-1,3-dioxane-2-yl]propyl]-3,5-dihydro-7-(o-fluorophenyl)-as-triazino[4,3-a][1,4]benzodiazepine-1,2-dione can be hydrolyzed in aqueous methanolic hydrogen chloride solution to give 10-chloro-3,5-dihydro-3-[3-(p-fluorobenzoyl)propyl]-7-(o-fluorophenyl)-as-triazino[4,3-a][1,4-]benzodiazepine-1,2-dione.

EXAMPLE 36

10-Chloro-3,5-dihydro-3-[3,3-di-(p-fluorophenyl)-propan-1-yl]-7-(o-fluorophenyl)-as-triazino[4,3-a][1,4]benzodiazepine-1,2-dione In the manner given in Example 4A, 10-chloro-3,5-dihydro-7-(o-fluorophenyl)-as-triazino[4,3-a][1,4]benzodiazepine-1,2-dione in dimethylformamide can be treated first with sodium hydride in mineral oil, and then with potassium iodide and 1,1-di(p-fluorophenyl)-3-chloropropane to give 10-chloro-3-[3,3-di-(p-fluorophenyl)-propan-1-yl]3,5-dihydro-7-(o-fluorophenyl)-as-triazino[4,3-a][1,4]benzodiazepine-1,2-dione.

EXAMPLE 37

2-[7-fluoro-5-(o-chlorophenyl)-3H-1,4-benzodiazepin-2-yl]hydrazide of oxalic acid ethyl ester In the manner given in Example 1 a solution of 7-fluoro-2-hydrazino-5-(o-chlorophenyl)-3H-1,4-benzodiazepine and triethylamine in tetrahydrofuran can be reacted at −80° C. with ethyl oxalyl chloride in tetrahydrofuran to give 2-[7-fluoro-5-(o-chlorophenyl)-3H-1,4-benzodiazepin-2-yl]hydrazide of oxalic acid ethyl ester.

EXAMPLE 38

9-Fluoro-3,5-dihydro-7-(o-chlorophenyl)-as-triazino[4,3-a][1,4]benzodiazepine-1,2-dione In the manner given in Example 2, a solution of 2-[7-fluoro-5-(o-chlorophenyl)-3H-1,4-benzodiazepin-2-yl]hydrazide of oxalic acid ethyl ester in pyridine can be heated to reflux to give 9-fluoro-3,5-dihydro-7-(o-chlorophenyl)-as-triazino[4,3-a][1,4]benzodiazepine-1,2-dione.

EXAMPLE 39

9-Fluoro-3,5-dihydro-3-methyl-7-(o-chlorophenyl)-as-triazino[4,3-a][1,4]benzodiazepine-1,2-dione In the manner given in Example 3, to a solution of 9-fluoro-3,5-dihydro-7-(o-chlorophenyl)-as-triazino[4,3-a][1,4]benzodiazepine-1,2-dione in tetrahydrofuran can be added sodium hydride and after 5 minutes methyl iodide dropwise. After stirring the mixture for 4 hours 9-fluoro-3,5-dihydro-3-methyl-7-(o-chlorophenyl)-as-triazino[4,3-a][1,4]benzodiazepine-1,2-dione is to be obtained.

EXAMPLE 40

2-[6-Bromo-5-(o-fluorophenyl)-3H-1,4-benzodiazepin-2-yl]hydrazide of oxalic acid ethyl ester In the manner given in Example 1, a solution of 6-bromo-2-hydrazino-5-(o-fluorophenyl)-3H-1,4-benzodiazepine and triethylamine in tetrahydrofuran can be reacted at −80° C. with oxalyl chloride in tetrahydrofuran to give 2-[6-bromo-5-(o-fluorophenyl)-3H-1,4-benzodiazepin-2-yl]hydrazide or oxalic acid ethyl ester.

EXAMPLE 41

8-Bromo-3,5-dihydro-7-(o-fluorophenyl)-as-triazino[4,3-a][1,4]benzodiazepine-1,2-dione In the manner given in Example 2, a solution of 2-[6-bromo-5-(o-fluorophenyl)-3H-1,4-benzodiazepine-2-yl]hydrazide of oxalic acid ethyl ester in pyridine can be heated to reflux to give 8-bromo-3,5-dihydro-7-(o-fluorophenyl)-as-triazino[4,3-a][1,4]benzodiazepine-1,2-dione.

EXAMLE 42

8-Bromo-3,5-dihydro-3-ethyl-7-(o-fluorophenyl)-as-triazino[4,3-a][1,4]benzodiazepine-1,2-dione In the manner given in Example 3, to a solution of 8-bromo-3,5-dihydro-7-(o-fluorophenyl)-as-triazino-[4,3-a][1,4]benzodiazepine-1,2-dione in tetrahydrofuran can be added sodium hydride and after 5 minutes ethyl iodide dropwise. After stirring the mixture for 4 hours 8-bromo-3,5-dihydro-3-ethyl-7-(o-fluorophenyl)-as-triazino[4,3-a][1,4]benzodiazepine-1,2-dione is obtained.

EXAMPLE 43

8-Bromo-3,5-dihydro-3-[3-(p-fluorobenzoyl)-propyl]-7-(o-fluorophenyl)-as-triazino[4,3-a][1,4]benzodiazepine-1,2-dione In the manner given in Example 4A, 8-bromo-3,5-dihydro-7-(o-fluorophenyl)-as-triazino[4,3-a][1,4]benzodiazepine-1,2-dione in dimethylformamide can be treated first with sodium hydride in mineral oil, and then with potassium iodide and 2-(3-chlorophenyl)-2-(p-fluorophenyl)-2,2-dimethyl-1,3-dioxane to give 8-bromo-3-[3[2-(p-fluorophenyl)-5,5-dimethyl-1,3-dioxane-2-yl]propyl]-3,5-dihydro-7-(o-fluorophenyl)-as-triazino[[4,3-a][1,4]benzodiazepine-1,2-dione.

In the manner given in Example 4B, 8-bromo-3-[3-[2(p-fluorophenyl)-5,5-dimethyl-1,3-dioxane-2-yl]propyl]-3,5-dihydro-7-(o-fluorophenyl)-as-triazino[4,3-a][1,4]benzodiazepine-1,2-dione can be hydrolyzed in aqueous methanolic hydrogen chloride solution to give 8-bromo-3,5-dihydro-3-[3-(p-fluorobenzoyl)-propyl] -7-(o-fluorophenyl)-as-triazino[4,3-a][1,4]benzodiazepine-1,2-dione.

EXAMPLE 44

2-[9-Trifluoromethyl-5-(2-pyridyl)-3H-1,4-benzodiazepin-2-yl]hydrazide of oxalic acid ethyl ester In the manner given in Example 1 a solution of 9-trifluoromethyl-2-hydrazino-5-(2-pyridyl)-3H-1,4-benzodiazepine and triethylamine in tetrahydrofuran can be reacted at −80° C. with ethyl oxalyl chloride in tetrahydrofuran to give 2-[9-trifluoromethyl-5-(2-pyridyl)-3H-1,4-benzodiazepin-2-yl]hydrazide of oxalic acid ethyl ester.

EXAMPLE 45

11-Trifluoromethyl-3,5-dihydro-7-(2-pyridyl)-as-triazino[4,3-a][1,4]benzodiazepine-1,2-dione In the manner given in Example 2, a solution of 2-[9-trifluoromethyl-5-(2-pyridyl)-3H-1,4-benzodiazepin-2-yl]hydrazide of oxalic acid ethyl ester in pyridine can be heated to reflux to give 9-trifluoromethyl-3,5-dihydro-7-(2-pyridyl)-as-triazino[4,3a]-[1,4]benzodiazepine-1,2-dione.

EXAMPLE 46

11-Trifluoromethyl-3,5-dihydro-3-methyl-7-(2-pyridyl)-as-triazino[4,3-a][1,4]-benzodiazepine-1,2-dione In the manner given in Example 3 to a solution of 0.002 mole of 11-trifluoromethyl-3,5-dihydro-3-methyl-7-(2-pyridyl)-as-triazino[4,3-a][1,4]benzodiazepine-1,2-dione in tetrahydrofuran can be added sodium hydride and after 5 minutes 0.0022 mole of methyl iodide dropwise. After stirring the mixture for 4 hours 11-trifluoromethyl-3,5-dihydro-3-methyl-7-(2-pyridyl)-as-triazino[4,3-a][1,4]benzodiazepine-1,2-dione is obtained.

EXAMPLE 47

2-[5-(o-Fluorophenyl)-3H-1,4-benzodiazepin-2-yl]hydrazide of oxalic acid ethyl ester In the manner given in Example 1, a solution of 2-hydrazino-5-(o-fluorophenyl)-3H-1,4-benzodiazepine and triethylamine in tetrahydrofuran can be reacted at −80° C. with ethyl oxalyl chloride in tetrahydrofuran to give 2-[5-(o-fluorophenyl)-3H-1,4-benzodiazepin-2-yl]-hydrazide of oxalic acid ethyl ester.

EXAMPLE 48

3,5-Dihydro-7-(o-fluorophenyl)-as-triazino-[4,3-a][1,4]benzodiazepine-1,2-dione

In the manner given in Example 2, a solution of 2-[5-(o-fluorophenyl)-3H-1,4-benzodiazepin-2-yl]hydrazide of oxalic acid ethyl ester in pyridine can be heated to reflux to give 3,5-dihydro-7-(o-fluorophenyl)-as-triazino[4,3-a[1,4]benzodiazepine-1,2-dione.

EXAMPLE 49

3,5-Dihydro-3-methyl-7-(o-fluorophenyl)-as-triazino[4,3-a[1,4]benzodiazepine-1,2-dione In the manner given in Example 3 to a solution of 3,5-dihydro-3-methyl-7-(o-fluorophenyl)-as-triazino[4,3-a][1,4]benzodiazepine-1,2-dione in tetrahydrofuran can be added sodium hydride and after 5 minutes methyl iodide dropwise. After stirring the mixture for 4 hours, 3,5-dihydro-3-methyl-7-(o-fluorophenyl)-as-triazino[4,3-a][1,4]benzodiazepine-1,2-dione can be obtained.

EXAMPLE 50

3,5-Dihydro-3-[3-(p-fluorobenzoyl)-propyl]7-(o-fluorophenyl)-as-triazino[4,3-a][1,4]benzodiazepine-1,2-dione In the manner given in Example 4A, 3,5-dihydro-(7-o-fluorophenyl)-as-triazino[4,3-a][1,4]benzodiazepine-1,2-dione in dimethylformamide can be treated first with sodium hydride in mineral oil, and then with 2-(3-chloropropyl)-2-(p-fluorophenyl)-2,2-dimethyl-1,3-dioxane to give 3-[3-[2-(p-fluorophenyl)-5,5-dimethyl-1,3-dioxane-2-yl]propyl]-3,5-dihydro-7-(o-fluorophenyl)-as-triazino[4,3-a][1,4]benzodiazepine-1,2-dione.

In the manner given in Example 4B, 3-[3-[2-(p-fluorophenyl)-5,5-dimethyl-1,3-dioxane-2-yl]propyl]-3,5-dihydro-7-(o-fluorophenyl)-as-triazino[4,3-a][1,4]benzodiazepine-1,2-dione can be hydrolyzed in aqueous methanolic hydrogen chloride solution to give 3,5-dihydro-3-[3-(p-fluorobenzoyl)-propyl]-7-(o-fluorophenyl)-as-triazino[4,3-a][1,4]benzodiazepine-1,2-dione.

In the manner given in Example 1, other 2-[5-phenyl-3H-1,4-benzodiazepin-2-yl]hydrazide of oxalic acid alkyl ester can be made. Representative compounds include:

2-[7-bromo-5-phenyl-3H-1,4-benzodiazepin-2-yl]-hydrazide of oxalic acid ethyl ester;

2-[9-bromo-5-(o-fluorophenyl)-3H-1,4-benzodiazepin-2-yl]hydrazide of oxalic acid methyl ester;

2-[9-nitro-5-(o-chlorophenyl)-3H-1,4-benzodiazepin-2-yl]hydrazide of oxalic acid ethyl ester;

2-[6-nitro-5-(o-fluorophenyl)-3H-1,4-benzodiazepin-2-yl]hydrazide of oxalic acid methyl ester.

2-[7-nitro-5-phenyl-3H-1,4-benzodiazepin-2-yl]-hydrazide of oxalic acid propyl ester;

3-ethyl-2-[6-trifluoromethyl-5-phenyl-3H-1,4-benzodiazepin-2-yl]hydrazide of oxalic acid methyl ester;

2-[8-fluoro-5-(o-chlorophenyl)-3-methyl-3H-1,4-benzodiazepin-2-yl]hydrazide of oxalic acid propyl ester;

2-[9-fluoro-5-(o-chlorophenyl)-3H-1,4-benzodiazepin-2-yl]hydrazide of oxalic acid ethyl ester;

2-[7-trifluoromethyl-5-phenyl-3H-1,4-benzodiazepin-2-yl]hydrazide of oxalic acid ethyl ester;

2-[6-chloro-5-phenyl-3H-1,4-benzodiazepin-2-yl]hydrazide of oxalic acid methyl ester; and the like.

In the manner given in Example 2, the 2-(5-phenyl-3H-1,4-benzodiazepin-2-yl)hydrazide of oxalic acid alkyl ester can be cyclized to give the corresponding 3,5-dihydro-7-phenyl-as-triazino[4,3-a][1,4]benzodiazepine-1,2-diones. Compounds, thus obtained, include:

9-bromo-3,5-dihydro-7-phenyl-as-triazino[4,3-a][1,4]-benzodiazepine-1,2-dione;

11-bromo-3,5-dihydro-7-(o-fluorophenyl)-as-triazino[4,3-a][1,4]benzodiazepine-1,2-dione;

11-nitro-3,5-dihydro-7-(o-chlorophenyl)-as-triazino[4,3-a][1,4]benzodiazepine-1,2-dione;

8-nitro-3,5-dihydro-7-(o-fluorophenyl)-as-triazino[4,3-a][1,4]benzodiazepine-1,2-dione;

9-nitro-3,5-dihydro-7-phenyl-as-triazino[4,3-a][1,4-benzodiazepine-1,2-dione;

8-trifluoromethyl-3,5-dihydro-5-ethyl-7-phenyl-as-triazino[4,3-a][1,4]benzodiazepine-1,2-dione;

10-fluoro-3,5-dihydro-5-methyl-7-(o-chlorophenyl)-as-triazino[4,3-a][1,4]benzodiazepine-1,2-dione;

11-fluoro-3,5-dihydro-7-(o-chlorophenyl)-as-triazino[4,3-a][1,4]benzodiazepine-1,2-dione;

9-trifluoromethyl-3,5-dihydro-7-phenyl-as-triazino[4,3a][1,4]benzodiazepine-1,2-dione;

8-chloro-3,5-dihydro-7-phenyl-as-triazino[4,3-a][1,4]benzodiazepine-1,2-dione, and the like.

These 3,5-dihydro-7-phenyl-as-triazino[4,3-a][1,2]benzodiazepines can be alkylated to give the corresponding 3-alkyl or 3-[ω-(diaryl)alkyl)] compounds, 3,5-dihydro-3-alkyl[ or 3-[ω-diaryl)alkyl]-7-phenyl-as-triazino[4,3-a][1,4]benzodiazepine-1,2-diones. Representative compounds, thus obtained, include:

9-bromo-3,5-dihydro-3-methyl-7-phenyl-as-triazino[4,3-a][1,4-benzodiazepine-1,2-dione;

11-bromo-3,5-dihydro-3-[[4,4-di(o-fluorophenyl)-butan]-1-yl]-7-(o-fluorophenyl)-as-triazino[4,3-a][1,4]-benzodiazepine-1,2-dione;

11-nitro-3,5-dihydro-3-methyl-7-(o-chlorophenyl)-as-triazino[4,3-a][1,4]benzodiazepine-1,2-dione;

8-nitro-3,5-dihydro-3-methyl-7-(o-fluorophenyl)-as-triazino[4,3-a][1,4]benzodiazepine-1,2-dione;

9-nitro-3,5-dihydro-3-methyl-7-phenyl-as-triazino[4,3-a][1,4]benzodiazepine-1,2-dione;

8-trifluoromethyl-3,5-dihydro-3-methyl-5-ethyl-7-phenyl-as-triazino[4,3-a][1,4]benzodiazepine-1,2-dione;

10-fluoro-3,5-dihydro-3,5-dimethyl-7-(o-chlorophenyl)-as-triazino[4,3-a][1,4]benzodiazepine-1,2-dione;

11-fluoro-3,5-dihydro-3-methyl-7-(o-chlorophenyl)-as-triazino[4,3-a][1,4]benzodiazepine-1,2-dione;

9-trifluoromethyl-3,5-dihydro-3-methyl-7-phenyl-as-triazino[4,3-a][1,4]benzodiazepine-1,2-dione;

8-chloro-3,5-dihydro-3-[[3,3-diphenylpropan]-1-yl]7-phenyl-as-triazino[4,3-a][1,4]benzodiazepine-1,2-dione;

9-bromo-3,5-dihydro-3-ethyl-7-phenyl-as-triazino[4,3-a][1,4]benzodiazepine-1,2-dione;

11-bromo-3,5-dihydro-3-ethyl-7-(o-fluorophenyl)-astriazino[4,3-a][1,4]benzodiazepine-1,2-dione;

11-nitro-3,5-dihydro-3-propyl-7-(o-chlorophenyl)-as-triazino[4,3-a][1,4]benzodiazepine-1,2-dione;

8-nitro-3,5-dihydro-3-ethyl-7-(o-fluorophenyl)-as-triazino[4,3-a][1,4]benzodiazepine-1,2-dione;

9-nitro-3,5-dihydro-3-ethyl-7-phenyl-as-triazino[4,3-a][1,4]benzodiazepine-1,2-dione;

8-trifluoromethyl-3,5-dihydro-3-isopropyl-7-phenyl-as-triazino[4,3-a][1,4]benzodiazepine-1,2-dione;

10-fluoro-3,5-dihydro-3-isopropyl-7-(o-chlorophenyl)-as-triazino[4,3-a][1,4]benzodiazepine-1,2-dione;

11-fluoro-3,5-dihydro-3-ethyl-7-(o-chlorophenyl)-as-triazino[4,3-a][1,4]benzodiazepine-1,2-dione;

9-trifluoromethyl-3,5-dihydro-3-propyl-7-phenyl-as-triazino[4,3-a][1,4]benzodiazepine-1,2-dione;

8-chloro-3,5-dihydro-3-ethyl-7-phenyl-as-triazino-[4,3-a][1,4]benzodiazepine-1,2-dione, and the like.

Following the procedures of Example 4A and 4B, the following compounds can be obtained:

9-bromo-3,5-dihydro-3-[3-(p-fluorobenzoyl)-propyl]penyl-as-triazino[4,3-a][1,4]benzodiazepine-1,2-dione;

11-bromo-3,5-dihydro-3-[3-(p-fluorobenzoyl)ethyl]7-(o-fluorophenyl)-as-triazino[4,3-a][1,4]benzodiazepine1,2-dione;

11-nitro-3,5-dihydro-3-[3-(m-fluorobenzoyl)propyl]-7-(o-chlorophenyl)-as-triazino[4,3-a][1,4]benzodiazepine-1,2-dione;

8-nitro-3,5-dihydro-3-[3-(p-fluorobenzoyl)propyl]-7-(o-fluorophenyl)-as-triazino[4,3-a][1,4]benzodiazepine-1,2-dione;

9-nitro-3,5-dihydro-3-[3-(p-fluorobenzoyl)propyl]-7-phenyl-as-triazino[4,3-a][1,4]benzodiazepine1,2-dione;

8-trifluoromethyl-3,5-dihydro-3-[3-(p-fluorobenzoyl)propyl]-7-phenyl-as-triazino[4,3-a][1,4]benzodiazepine-1,2-dione;

10-fluoro-3,5-dihydro-3-[3-(o-fluorobenzoyl)propyl]-7-(o-chlorophenyl)-as-triazino[4,3-a][1,4]benzodiazepine-1,2-dione;

11-fluoro-3,5-dihydro-3-[3-(p-chlorobenzoyl)propyl]-7-(o-chlorophenyl)-as-triazino[4,3-a][1,4]benzodiazepine-1,2-dione;

9-trifluoromethyl-3,5-dihydro-3-[3-(p-fluorobenzoyl)-propyl]-7-phenyl-as-triazino[4,3-a][1,4]benzodiazepine-1,2-dione;

8-chloro-3,5-dihydro-3-[3-benzoylpropyl]-7-phenyl-as-triazino[4,3-a][1,4]benzodiazepine-1,2-dione; and the like.

Treating the compounds of formula V with pharmacologically acceptable acids as hydrochloric, hydrobromic, phosphoric, sulfuric, acetic, propionic, toluenesulfonic, methanesulfonic, tartaric, citric, lactic, malic, maleic, and cyclohexanesulfamic acids produces the pharmacologically acceptable salts of these compounds of formula V which can be used like the free base compounds of formula V. Salt formation is achieved in conventional manner by reacting the compounds of formula V with excess of a selected acid in a suitable medium, e.g., water, a lower alkanol, ether, or acetone and recovering the salt by evaporating the solvent, preferably in vacuo.

I claim:

1. A compound of the formula V:

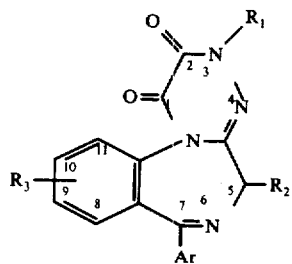

wherein $R_1$ is hydrogen, alkyl of 1 to 3 carbon atoms, inclusive,

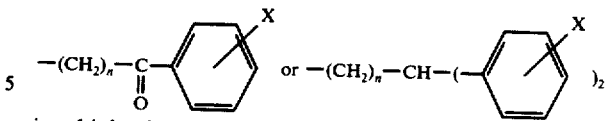

in which $n$ is 2 or 3, and X is hydrogen, fluoro or chloro; wherein $R_2$ is hydrogen, methyl or ethyl; wherein $R_3$ is hydrogen, fluoro, chloro, bromo, trifluoromethyl and nitro; and wherein Ar is phenyl, o-chlorophenyl, o-fluorophenyl, 2,6-difluorophenyl or 2-pyridyl or the pharmacologically acceptable acid addition salts thereof.

2. A compound according to claim 1 wherein $R_1$ is [3-(p-fluorobenzoyl)propyl], $R_2$ is hydrogen, $R_3$ is 9-chloro, Ar is phenyl and the compound is 9-chloro-3,5-dihydro-3-[3-(p-fluorobenzoyl)propyl]-7-phenyl-as-triazino[4,3-a][1,4]benzodiazepine-1,2-dione.

3. A compound according to claim 1 of the formula:

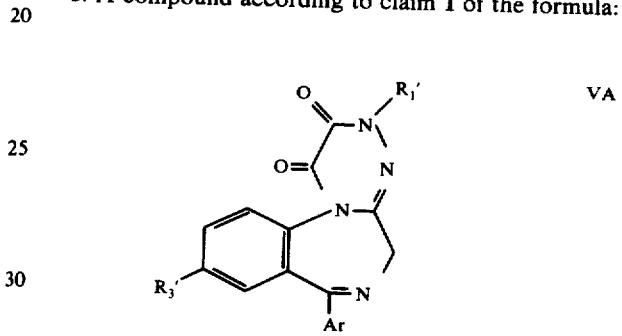

$R_1'$ is hydrogen or alkyl of 1 to 3 carbon atoms, inclusive; wherein $R_3'$ is fluoro, chloro, bromo, or trifluoromethyl; and wherein Ar is phenyl, o-chlorophenyl, o-fluorophenyl, 2,6-difluorophenyl or 2-pyridyl, or the pharmacologically acceptable acid addition salts.

4. The compound of claim 3 wherein $R_1'$ is hydrogen, $R_3'$ is bromo, Ar is 2-pyridyl, and the compound is therefore 9-bromo-3,5-dihydro-7-(2-pyridyl)-as-triazino[4,3-a][1,4]benzodiazepine-1,2-dione.

5. A compound according to claim 1 of the formula VB:

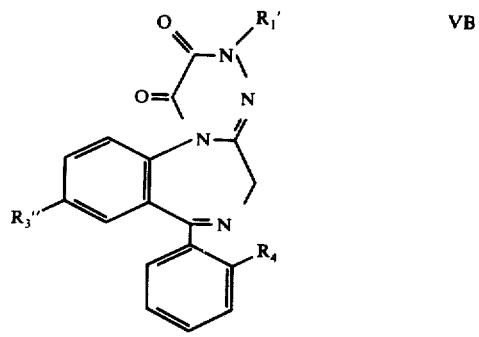

wherein $R_1'$ is hydrogen or alkyl of 1 to 3 carbon atoms, inclusive, wherein $R_3''$ is fluoro, chloro or trifluoromethyl; and wherein $R_4$ is hydrogen, chloro or fluoro, or the pharamacologically acceptable acid addition salts thereof.

6. A compound according to claim 5 wherein $R_1'$ and $R_4$ are hydrogen, $R_3''$ is chloro, and the compound is therefore 9-chloro-3,5-dihydro-7-phenyl-as-triazino[4,3-a][1,4]benzodiazepine-1,2-dione.

7. A compound according to claim 5 wherein $R_1'$ is methyl, $R_4$ is hydrogen, $R_3''$ is chloro and the compound is therefore 9-chloro-3,5-dihydro-3-methyl-7-phenyl-as-triazino[4-3-a][1,4]benzodiazepine-1,2-dione.

8. A compound according to claim 5 wherein $R_1'$ is hydrogen, $R_3''$ and $R_4$ are chloro and the compound is therefor 9-chloro-3,5-dihydro-7-(o-chlorophenyl)-as-triazino-[4,3-a][1,4]benzodiazepine-1,2-dione.

9. A compound according to claim 5 wherein $R_1'$ is hydrogen, $R_3''$ is hydrogen, $R_4$ is chloro, and the compound is therefore 3,5-dihydro-7-(o-chlorophenyl)-as-triazino-[4,3-a][1,4]benzodiazepine-1,2-dione.

10. A compound according to claim 5 wherein $R_1'$ is methyl, $R_3''$ and $R_4$ are chloro, and the compound is therefore, 9-chloro-3,5-dihydro-3-methyl-7-(o-chlorophenyl)-as-triazino[4-3-a][1,4]benzodiazepine-1,2-dione.

* * * * *